United States Patent [19]

Affeldt et al.

[11] Patent Number: 4,838,277
[45] Date of Patent: Jun. 13, 1989

[54] VASOMETRIC TEST APPARATUS FOR FINGER TESTING

[75] Inventors: Karl-Heinz Affeldt; Ulrich Hantel, both of Berlin, Fed. Rep. of Germany

[73] Assignee: Robert Bosch GmbH, Stuttgart, Fed. Rep. of Germany

[21] Appl. No.: 194,462

[22] Filed: May 16, 1988

[30] Foreign Application Priority Data

May 21, 1987 [DE] Fed. Rep. of Germany ....... 3717045

[51] Int. Cl.⁴ ............................................. A61B 5/02
[52] U.S. Cl. .................................... 128/691; 128/666; 128/687
[58] Field of Search ............... 128/663, 637, 664, 665, 128/666, 667, 672, 687, 691, 694, 774, 779, 782, 26

[56] References Cited

U.S. PATENT DOCUMENTS 4,183,360  1/1980  Carlson et al. ...................... 128/666
4,425,922  1/1984  Conti et al. ......................... 128/691
4,509,528  4/1935  Sahota ................................ 128/691

FOREIGN PATENT DOCUMENTS 2524792  10/1983  France ................................ 128/664

Primary Examiner—Max Hindenburg
Assistant Examiner—John D. Zele
Attorney, Agent, or Firm—Frishauf, Holtz, Goodman & Woodward

[57] ABSTRACT

To permit loose and relaxed position of the hand of a patient over a vasometric apparatus, the apparatus is formed in the shape of a hollow domed housing within which a volume pulse sensor (30) is located, retained with resiliently adjustable bias force such that the sensing surface (33) of the volume pulse sensor extends just slightly above the outer surface of the domed housing. The spring force with which the sensor engages a finger (45) of the patient is adjustable by an externally adjustable disk or wheel (37).

11 Claims, 1 Drawing Sheet

VASOMETRIC TEST APPARATUS FOR FINGER TESTING

Reference to related application by the inventor hereof and assigned to the assignee of the present invention, the disclosure of which is hereby incorporated by reference:

U.S. Ser. No. 07/194,463, filed May 16, 1988, AFFELDT et al.

REFERENCE TO RELATED PUBLICATION

Prof. Völker, "Herz- and Gefässerkrankungen", Kreislaufbücherei English translation by H. Mayer, M.D., Stanford University, "Cardiac and Vascular Disorders", published by Charles C. Thomas, Copyright 1965.

The present invention relates to vasometric test apparatus, and more particularly to such apparatus to test interferences with blood flow by means of vasography.

BACKGROUND

Testing for interference with blood circulation is known, see the publication Prof. Völker, "Cardiac and Vascular Disorders" (English translation by Henry Mayer, M.D., published by Charles C. Thomas, second edition, Copyright 1965). The apparatus used is usually termed vasometric apparatus, to determine such interferences by vasography. A light sensor, which may be responsive to transmitted or reflected light is applied, for example, to a digit of the person to be tested. The sensor is responsive to check the volume pulse of blood flow and provide representative electrical signals. The electrical signals, after amplification, are then displayed on a display monitor as a curve, or recorded on a curve drawing recording instrument. Curves are obtained from the right as well as the left side of the person to be tested, and upon comparison of the curves of similar digits, it is possible to determine the condition of blood vessels.

The measuring method described is subject to errors, in that the measuring result depends on the sensor as applied to the digit of the person to be tested, as well as the maintenance of the digit in quiet and relaxed condition while the measuring takes place.

The digits to be tested may be the fingers or the toes of the person to be tested.

THE INVENTION.

It is an object to provide an apparatus which retains the fingers of a hand in loose, relaxed and yet fixed position, while retaining a sensor against the finger with only small mechanical bias or pressure, so that the expansion of blood vessels, and particularly small artery vessels is not affected by the testing apparatus.

Briefly, the apparatus includes a domed housing, for example an essentially hemispherical element. The domed housing forms a support for the handl of the patient, so that the patient can place and cup the hand thereover while being fully relaxed. A volume pressure sensor is located in the housing. The housing is formed with an opening to permit the volume pressure sensor to extend therethrough such that a sensing surface thereof projects just slightly outside of the outer surface of the domed housing. The volume pulse sensor is resiliently secured within the housing. and preferably such that the resilient force with which the sensor is extended outside of the housing is adjustable. Thus, only a minimum, and adjustable pressure by the finger of the patient against the sensing surface need be required to still obtain accurate and reproducible measurements.

The apparatus has the advantage that the patient can slightly curl the hand, thus leave the hand in fully relaxed condition. The position of the finger about the domed housing can be retained without change. The resilient support of the sensor provides only minimum and adjustable counter force or engagement force against the finger.

Drawings showing an illustrative embodiment:

FIG. 1 is a vertical sectional view through the housing, and illustrating the sensor apparatus within the housing; and FIG. 2 is a fragmentary top view of the apparatus.

DETAILED DESCRIPTION

Figure 1:
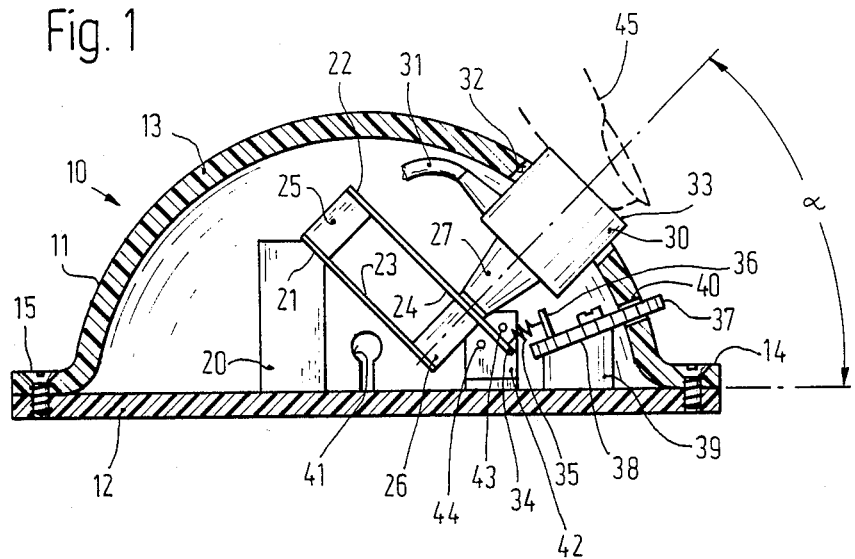
Figure 2:
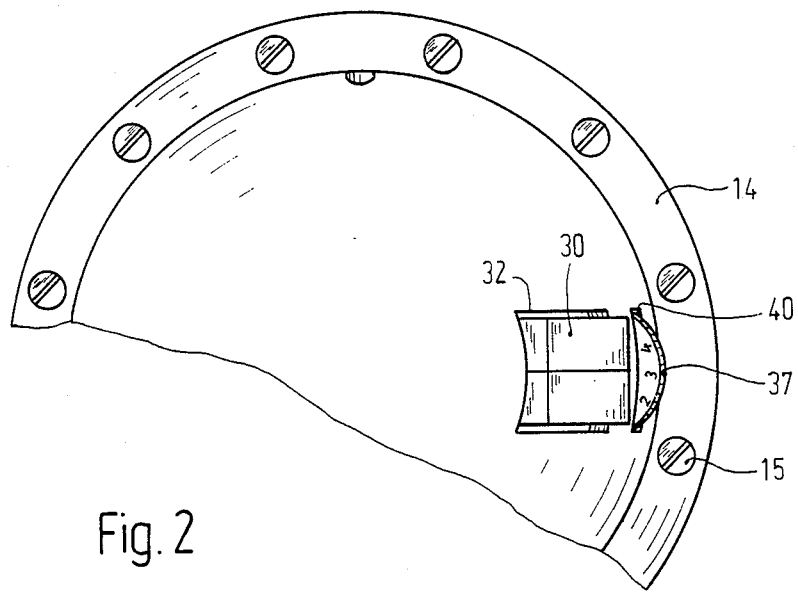

The apparatus 10 has a housing 11 which includes a dome-shaped cap or cover 13 and a circular base plate 12. The dome-shaped cap or cover is, preferably, essentially hemispherical, but may have other configurations. Cap 13 and base plate 12 define a hollow space. An external edge or flange 14 of the cap 13 is secured by screws 15 to the base plate 12. Screws 15, preferably, are uniformly distributed about the circumference of the base plate. A sensor support 20 is mounted on the base plate 12. Support 20 has an inclined face 21 at an upper end thereof on which a resilient or spring support element is secured. The resilient or spring support element is formed of two elongated leaf springs 23, 24. securely coupled together at their ends by spacers 25, 26. The end of the resilient element 22 which is remote from the support 21 has a holder 27 attached thereto on which an essentially lock-like volume pulse sensor 30 is located. Preferably, the sensor is a reflection light sensor. An electrical cable 31 extends from the sensor 30. The sensor 30 may include a light source, and photosensitive elements responsive to reflective light from a finger 45 of the patient. The sensor 30 extends through an opening 32 of the dome-shaped cap 13. The outer sensor surface 33 projects slightly above the outer surface of the cap 13. The angle $\alpha$ between the longitudinal axis of the sensor 30 and the plane of the base 12 is, preferably, in the range of between 40° and 60°. The angle is not critical.

The upper leaf spring 24 of the spring element 22 is slightly longer than the lower leaf spring 23 to form an extension 34 to which an end of a further spring 35 is secured. Spring 35 is a tension spring which is coupled at the end remote from the extension 34 to a pin 36 which is coupled to an adjustment disk 37. The adjustment disk 37 is located on an inclined surface 38 of a support block 39, rotatable with respect thereto, and extends with a portion of its circumference through a slitlike opening 40 in the cap 13, to permit adjustment, in steps or continuously, from the outside, to thereby adjust the tension being applied by the spring 35 on the leaf spring or resilient support 22.

The deflecting movement of the volume pulse sensor is limited by adjustment stops 43, 44, located on both sides of the extension 34, and retained on a bracket 42, secured to the base plate 12. In quiescent condition, tension element 22 retains the sensor 30 so that the extension 34 is in engagement with the upper stop 43.

The connection cable 30 is conducted towards the outside through an opening 41. Preferably, a strain relief is connected to the cable 31 before being passed to the outside.

OPERATION

A patient, preferably lying on an examination table or the like, extends the arms laterally of the body and cups the hands over the structures 10, on either side of the body, in such a manner that a finger 45 (FIG. 1), and preferably the middle finger, loosely and in a relaxed manner engages the sensor surface 33. The projecting force or resilient or spring force of the spring 35 is adjusted by rotating the adjustment disk 37 such that only a very slight pressure is exerted by the volume pulse sensor against the surface of the finger 45. The cable 31 is coupled to a display element and to a current source. The volume pulse sensor then converts volume pulses of blood flow and blood vessels of the finger 45 of the patient into corresponding electrical signals which can be recorded on a strip recorder and displayed on a display monitor.

Various changes and modifications may be made within the scope of the inventive concept. For example, the housing may be made of various materials and, in accordance with a preferred embodiment, is made of a heat insulating or low heat transferring plastic material.

We claim:

1. Vasometric test apparatus for testing blood supply to a finger (45) of a patient, comprising
    a domed housing (11) defining an outer surface and forming a support for the hand of the patient;
    a pulse sensor (30) having a sensing surface (33), said sensor being retained in the housing, the housing being formed with an opening (32) to permit the pulse sensor to extend therethrough; and
    resilient means (22, 35) securing the pulse sensor in the housing such that the sensing surface (33) projects slightly above the outer surface of the domed housing to permit engagement of the finger of a patient with said testing surface while the hand of the patient is cupped over the domed housing, whereby the volume of blood supplied to the finger is sensed.

2. The apparatus of claim 1, wherein the housing comprises a base plate (12) and an essentially hemispherical cap (13) secured to the base plate.

3. The apparatus of claim 1, wherein the pulse sensor (30) defines a longitudinal axis;
    and said longitudinal axis is positioned at an angle of between about 40° to 60° with respect to a plane coplanar with the base plate.

4. The apparatus of claim 1, wherein the pulse sensor (30) is a reflection light sensor.

5. The apparatus of claim 1, wherein the resilient means comprises an elongated spring element (22) having one end secured within the housing and the other end connected to the pulse sensor for resiliently deflectably supporting the pulse sensor.

6. The apparatus of claim 5, wherein the elongated spring element comprises two elongated leaf spring (23, 24) arranged parallel to each other;
    and spacer means (25, 26) retaining said leaf springs in spaced, parallel position.

7. The apparatus of claim 5, including stop means (42, 43, 44) limiting the deflection of the spring means and hence of the pulse sensor.

8. The apparatus of claim 1, wherein the resilient means include means (36, 37) for adjusting the resilience force for retaining the pulse sensor in a position projecting slightly above the outer surface of the domed housing.

9. The apparatus of claim 8, wherein the adjustment means comprises an adjustment disk (37) and a spring element (35) coupled to the pulse sensor (30) and adjustably biasing the pulse sensor to said slightly projecting position above the outer surface of the domed housing, said adjustment disk being accessible externally from the domed housing.

10. The apparatus of claim 1, further including cable means (31) coupled to the pulse sensor (30);
    and wherein the housing is formed with a cable exit opening (41) for permitting strain-relieved passage of the cable to the outside of the housing.

11. The apparatus of claim 1, wherein said domed housing comprises a heat insulating plastic material.

* * * * *